United States Patent [19]

Oeser et al.

[11] 4,066,549
[45] Jan. 3, 1978

[54] APPARATUS FOR THE PRECIPITATION OF HUMAN BLOOD PLASMA COMPONENTS

[75] Inventors: Henning C. Oeser, Duisburg; Ulrich Ahrens, Springe, both of Germany

[73] Assignee: Blutspendedienst der Landesverbande des Deutschen Roten Kreuzes Niedersachsen, Oldenburg und Bremen GmbH, Germany

[21] Appl. No.: 614,419

[22] Filed: Sept. 18, 1975

[30] Foreign Application Priority Data

Sept. 18, 1974 Germany ............... 2444524

[51] Int. Cl.$^2$ .................. C07G 7/00; B03D 3/02; A23J 1/06

[52] U.S. Cl. .................. 210/177; 23/258.5 R; 210/45; 210/179; 210/181; 210/201; 210/206; 210/254; 210/257 R; 210/DIG. 23; 260/112 B

[58] Field of Search ............. 23/258.5 R; 260/112 B; 210/201, 206, 254, 257 R, 177, 179, 181, 45, DIG. 23

[56] References Cited

U.S. PATENT DOCUMENTS

| | | | |
|---|---|---|---|
| 2,470,332 | 5/1949 | Bollaert et al. | 210/206 X |
| 2,632,733 | 3/1953 | Sherwood | 210/201 X |
| 3,536,450 | 10/1970 | Dus et al. | 23/253 R |
| 3,698,870 | 10/1972 | De Jong | 23/253 R |
| 3,764,009 | 10/1973 | Watt | 210/DIG. 23 X |

OTHER PUBLICATIONS

Callaham, J. R.; "Engineering Technique Commercializes Human Blood Fractionation,"; C & M.E., June 1946, pp. 101-103.

*Primary Examiner*—Barry S. Richman
*Attorney, Agent, or Firm*—Shlesinger, Arkwright, Garvey & Dinsmore

[57] ABSTRACT

A process and apparatus for the precipitation of human blood plasma components characterized in that the initial blood plasma and the precipitating agent are continuously introduced into a precipitation container in an adjusted relationship but separated with simultaneous control of the required pH values. The suspension of the individual precipitants is conveyed across a delay station and then separated. The delay station includes a flow passageway connecting the precipitation container to a separating means, with the flow passageway being so constructed as to permit substantially laminar flow of fluid therethrough. Means are also present in the flow passageway for changing the residence time of fluid therein by permitting selective variation of the length of the flow passageway.

4 Claims, 1 Drawing Figure

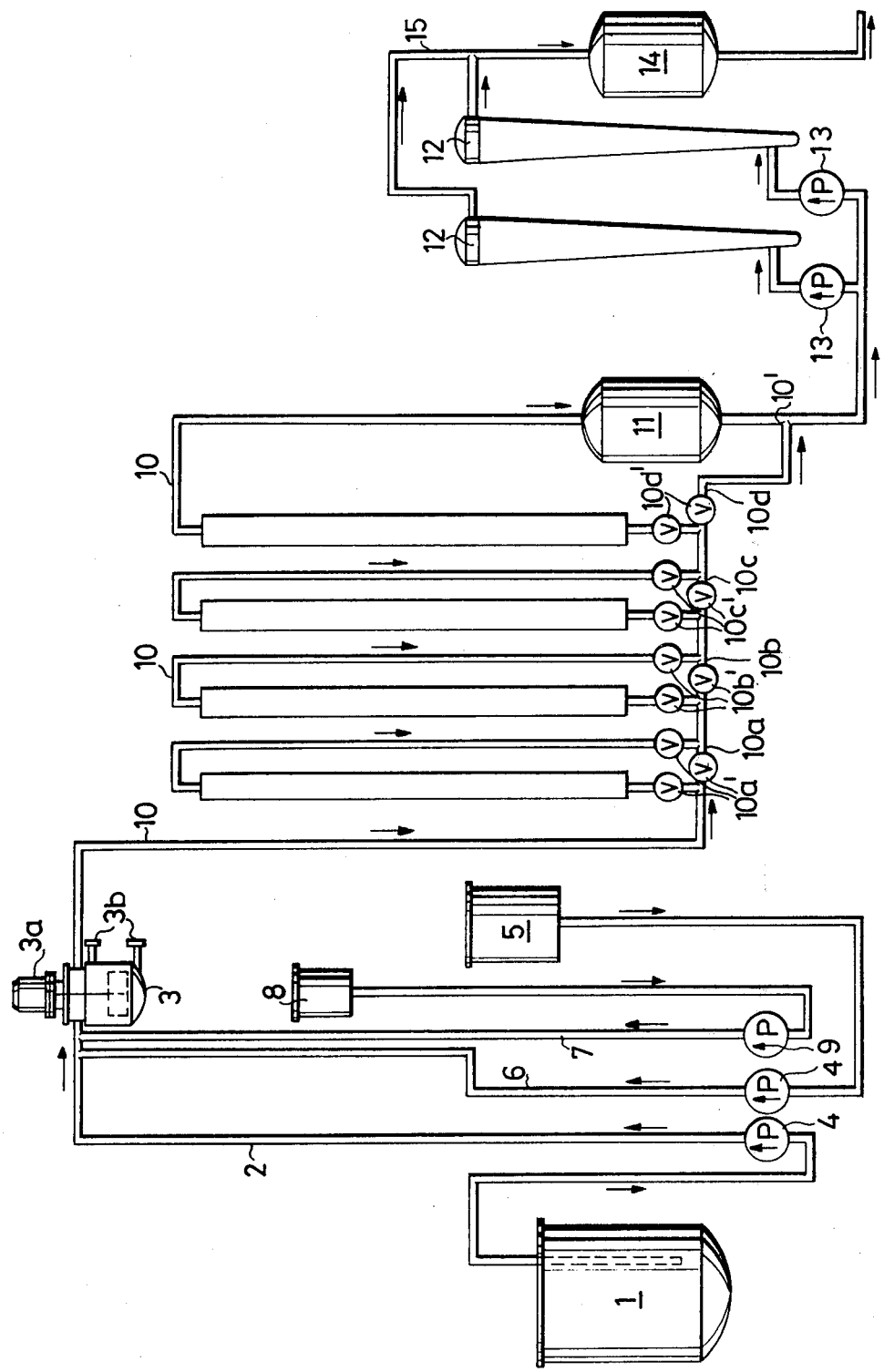

APPARATUS FOR THE PRECIPITATION OF HUMAN BLOOD PLASMA COMPONENTS

This invention relates to a method and apparatus for the precipitation of human blood plasma components. More specifically, the invention deals with the continuous precipitation of human blood plasma components.

BACKGOUND AND OBJECTS

The precipitation of human blood plasma components has been carried out for many years on a technical scale in order to extract the therapeutically valuable albumin components from it. Such components are principally fibrinogens with coagulation factors, albumin, and immunoglobulins. Thus, the prior art processes have been fractional precipitation processes whereby the albumin components in question are caused to precipitate under the required conditions of pH, ion strength, and ethyl alcohol concentration. The use of ethyl alcohol as a precipitating agent requires, furthermore, that the procedure be conducted at temperatures below 0° C in order to protect the albumin from denaturation.

In general, the precipitation is carried out at a temperature range of about 0° C to −8° C at a pH range of about 4–7 with an ethyl alcohol concentration at a maximum of about 40% by volume. The ethyl alcohol is added very slowly with constant cooling, and in addition, regulating reagents or buffers are added to maintain the pH value. As soon as a precipitate which is ready for separation has formed, the precipitate is separated over cylindrical centrifuges by filtration or other suitable means, and the remaining liquid is subjected to a further precipitation followed by filtration or centrifugation. The procedure is repeated until the fractional precipitation is complete.

The prior art procedures of this type obviously work in a discontinuous manner. Accordingly, a certain amount of blood plasma was first merely precipitated and left in the precipitation receptacle for a period of time until the precipitate had formed sufficiently to be ready for separation. It is quite clear, then, that this prior art procedure is very uneconomical and inefficient. Therefore, a primary object of this invention is to develop a procedure for the precipitation of human blood plasma components which can operate continuously. To accommodate this objective, a procedure is proposed in which the initial blood plasma as well as the precipitating agent is conveyed to a precipitation receptacle in an adjusted, checked relationship continuously, yet separated under simultaneous control of the necessary pH values. In this case, the suspension is led over a delay area for the agglomeration of the individual components of the precipitate, and is then separated. It is obvious that according to this invention, the accomplishing of the precipitation reaction and the delay duration of the suspension have, according to this procedure, been separated, so that in this way, a continuous conveying of new blood plasma into the precipitation container is possible.

According to a further procedural characteristic of this invention, care is taken that the precipitation results in turbulence in the receptacle while the suspension flows though the delay area with approximate laminar flow.

As far as a fractional precipitation --as mentioned at the outset-- is desired, it is seen according to the invention procedure that after the separation, the remaining blood plasma is subjected anew to an appropriate treatment. As no closer explanation is necessary, this can result from corresponding similar devices connected in series.

One single arrangement according to the invention consists preferably of supply containers for the blood plasma, the precipitating agent, and the pH regulating agents, which are connected over separate feed pipes with the precipitation container, and each includes a pump in the feed pipes. There is also a correspondingly long discharge duct or pipe placed on the precipitation holder as the delay component and is connected with a separate piece of equipment, preferably with a centrifuge.

In order to accommodate the discharge pipe as efficiently as possible, despite its considerable length, the invention further provides that the discharge pipe is arranged in a sinusoidal or other form. With this type of arrangement, it is possible in a simple manner to provide for by-pass pipes which enable a shortening of the delay length. Such a shortening can result in ¼, ½ or ¾ of the total length. The possibility for such a reduction has the advantage that the flowing of the fluid components through the device can be varied according to required circumstances. Thus, it becomes possible to detour a part of the pipe length by eliminating portions of the piping from the flow path. Corresponding to the amount of piping in the fluid circuit, the detour is brought about so that the flow of the fluid from the apparatus can be reduced as indicated above to ¾, ½ or ¼ without changing the delay time of the suspension within the delay region.

According to a further characteristic of this invention, an intermediate container is provided and inserted into the discharge pipe. Such intermediate container has the advantage that in the case of a stationary centrifuge, the device itself can continue operation since the suspension is coming out of the delay region and is collected in the intermediate holding device.

Finally, according to the invention, a collecting receptacle for the centrifugate of the centrifuge is provided. Again, this collecting receptacle can be used in a similar manner as the supply container for the blood plasma already mentioned, insofar as a fractional precipitation is carried out. For the same device with a precipitation container, a delay region connects to the collecting container. Depending on the desired fractions, two or more devices can be connected behind one another without difficulty.

Specifically, according to the invention, the precipitation receptacle itself has circulation cooling with automatic temperature control in order to obtain optimal precipitation conditions. For the same reason, it is also desireable to provide for an agitator in the precipitation container.

In the accompanying drawings, a flow sheet of the process is schematically presented.

A supply container 1 is provided for the blood plasma being treated, and is connected by a feed pipe 2 with a precipitation container 3. The blood is continuously pumped by an adjustable pump 4 through the feed pipe 2 into the precipitation container 3. The pump 4 can also be used as a 2-component pump so that it simultaneously supplies the precipitation agent, ethyl alcohol.

The precipitation agent is located in a supply container 5, and the precipitating agent is conveyed through the pipe line 6 toward the precipitating container 3, but the precipitating agent is introduced into the pipe line 2 immediately before the precipitation container. An additional pipe line 7 extends from receptacle 8 to the pipe line 2 immediately before the precipitation container. The receptacle 8 contains the pH regulating agent or buffer which is pumped by means a pump 9. Suitable automatic controls may be utilized to operate the pump 9 so as to maintain the required pH control within the precipitation container 3.

The precipitation container 3 is provided with an agitator 3a and also with a circulation cooler (not shown). The connection of the circulation cooler occurs at the connections 3b. The actual water jacket is located in a cylindrical container surrounding the precipitation vessel 3. The cooling serves to provide a constant precipitation temperature within the receptacle 3, since the process is an exothermic process.

The precipitation receptacle 3 is provided with a discharge pipe 10 from which the precipitation suspension continuously flows. The discharge pipe 10 is formed relatively long so that an agglomeration of the separated individual components can occur during the flow through of the suspension. In this discharge pipe 10 which serves as the delay region-in contrast to the precipitation container- laminar flow relationships dominate.

The discharge pipe 10 is conducted in a sinusoidal or similar tortuous path whereby the individual components are excluded across the detour pipes 10a, 10b, 10c and 10d, as well as the accompanying valves 10a', 10b', 10c' and 10d', and the entire length may be thereby reduced to ¼, ½ and ¾, according to the requirements.

The discharge pipe 10 terminates in an intermediate container 11 which also serves as a type of compensation container in the event that the centrifuges 12, which are connected across the extended discharge pipe 10 with the intermediate container 11, are disconnected, but the device continues on the input side.

Within the outlet pipes 10 or 10' are provided metering pumps 13 for the centrifuges 12.

The centrifugate, i.e. the remaining fluid part, passes through the centrifuges 12 into a gathering container 14 by means of a connecting pipe 15. The gathering container 14 forms a supply container insofar as fractional precipitation is carried out, similar to the supply container 1, for the next precipitation. Thus the supply container 14 is connected to a further precipitation container similar to container 3 which is also provided with a supply for the precipitating agents and the buffering component.

The advantages of the present invention are quite clear. For example, several similar devices can be combined under an intermediate switch position of centrifuges or other continuously working separable arrangements, and the fractional precipitation of plasma from the beginning to the end of the process can be accomplished in a continuous manner. By connecting two such similar devices, the possibility exists for the simultaneous execution of two fractional precipitations, and the advantage thereby of the continuous manner of operation.

While this invention has been described, it will be understood that it is capable of further modification, and this application is intended to cover any variations, uses and/or adaptations of the invention following in general, the principle of the invention and including such departures from the present disclosure as come within known or customary practice in the art to which the invention pertains, and as may be applied to the essential features hereinbefore set forth, as fall within the scope of the invention or the limits of the appended claims.

What is claimed is:

1. An apparatus for the continuous precipitation of human blood plasma components comprising:

individual supply containers for blood plasma, a precipitation agent and a buffer solution, a precipitation vessel, means for conveying the blood plasma and the precipitation agent from the respective supply containers to said precipitation vessel and including means for combining the blood plasma and precipitating agent immediately upstream of said precipitation vessel, means for conveying the buffer solution from its respective supply container to said precipitation vessel, means for cooling said precipitation vessel and the contents thereof, means for causing turbulence in said precipitation vessel, a flow passageway connecting said precipitation vessel and centrifuge means, said flow passageway being so constructed as to permit substantially laminar flow of fluid therethrough, means for selectively changing the residence time of fluid in said flow passageway by varying the length of said flow passageway through which fluid is caused to flow, and means for removing the centrifugate from said centrifuge means.

2. An apparatus as in claim 1 and wherein:

said flow passageway is arranged in a sinusoidal path and includes valve means for selecting that portion of the flow passageway through which fluid may flow.

3. An apparatus as in claim 2 and including:

an intermediate container provided near the end of said flow passageway and means connecting said intermediate container and said centrifuge means.

4. An apparatus as in claim 2 and including:

a centrifugate receiving container connected to said centrifuge means, a second said apparatus for precipitation of human blood plasma components connected in series, said centrifugate receiving container of the first apparatus comprising the blood plasma supply container for the second apparatus.

* * * * *